(12) United States Patent
Stahl et al.

(10) Patent No.: US 11,795,142 B2
(45) Date of Patent: Oct. 24, 2023

(54) METHOD FOR PREPARING GUANIDINO ACETIC ACID

(71) Applicant: Evonik Operations GmbH, Essen (DE)

(72) Inventors: Timo Stahl, Limeshain (DE); Axel Ronneburg, Hanau (DE); Philipp Roth, Hanau (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 18/043,572

(22) PCT Filed: Aug. 18, 2021

(86) PCT No.: PCT/EP2021/072929
§ 371 (c)(1),
(2) Date: Feb. 28, 2023

(87) PCT Pub. No.: WO2022/048909
PCT Pub. Date: Mar. 10, 2022

(65) Prior Publication Data
US 2023/0295078 A1    Sep. 21, 2023

(30) Foreign Application Priority Data
Sep. 1, 2020 (EP) .................................. 20193773

(51) Int. Cl.
*C07C 279/14* (2006.01)
(52) U.S. Cl.
CPC .................................. *C07C 279/14* (2013.01)
(58) Field of Classification Search
CPC .................................................... C07C 279/14
USPC ........................................................ 560/560
See application file for complete search history.

(56) References Cited

U.S. PATENT DOCUMENTS

| 10,844,009 B2 | 11/2020 | Stahl et al. |
| 2011/0257075 A1 | 10/2011 | Gastner et al. |
| 2020/0207707 A1 | 7/2020 | Stahl et al. |

FOREIGN PATENT DOCUMENTS

| CN | 101462983 | 6/2009 |
| CN | 102329250 | 1/2012 |
| EP | 3 677 329 | 7/2020 |
| WO | 2005/120246 | 12/2005 |

OTHER PUBLICATIONS

Buchanan et al. "The Hydrolysis and Polymerization of Cyanamide in Alkaline Solutions" Alkaline Hydrolysis of Cyanamide, vol. 52, Jan. 8, 1930, pp. 195-206.
Extended European Search Report dated Mar. 11, 2021, in European Application No. 20193773.7, 9 pages.
Humm et al., "Recombinant expression and isolation of human L-arginine:glycine amidinotransferase and identification of its active-site cysteine residue", Biochem. J., vol. 322, 1997, pp. 771-776.
International Search Report dated Dec. 2, 2021, in PCT/EP2021/072929, 6 pages.
M. Strecker, comptes rendus 1861, 52, 1212, cited in: Ber. Chem. Ges. (now: Eur. J. Inorg. Chem.), 1908, 41, pp. 4385.
Written Opinion dated Dec. 2, 2021, in PCT/EP2021/072929, 8 pages.

*Primary Examiner* — Ana Z Muresan
(74) *Attorney, Agent, or Firm* — Grüneberg and Myers PLLC

(57) ABSTRACT

A modified method for preparing guanidino acetic acid (GAA) involves reacting cyanamide with an excess molar amount of glycine in an aqueous reaction mixture, in the presence of a base. The method avoids high molar amounts of base or acid for pH control, and maintains the reaction selectivity and product yields.

3 Claims, 2 Drawing Sheets

FIG. 1: Fed Batch
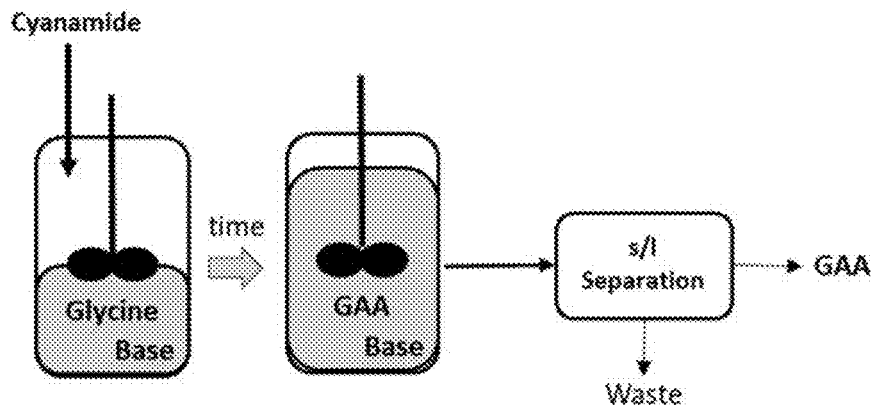
FIG. 2: Continuously operated reaction system
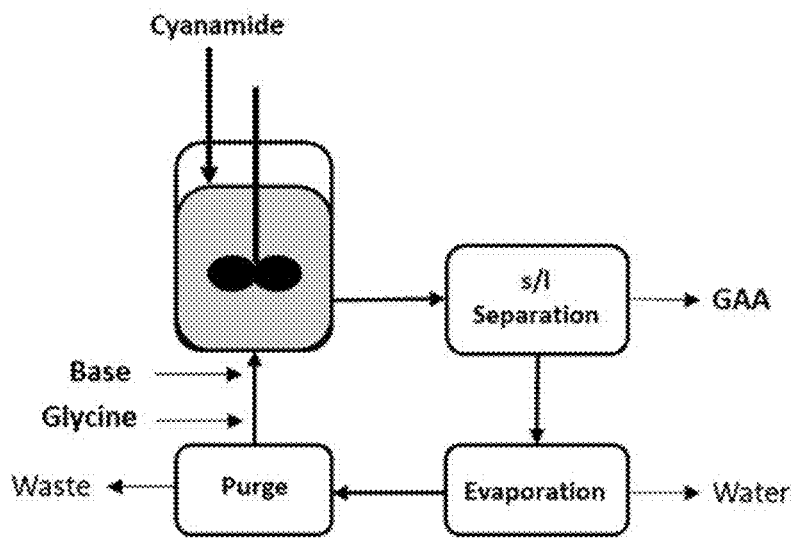
FIG. 3: Fed Batch Concept according to the invention
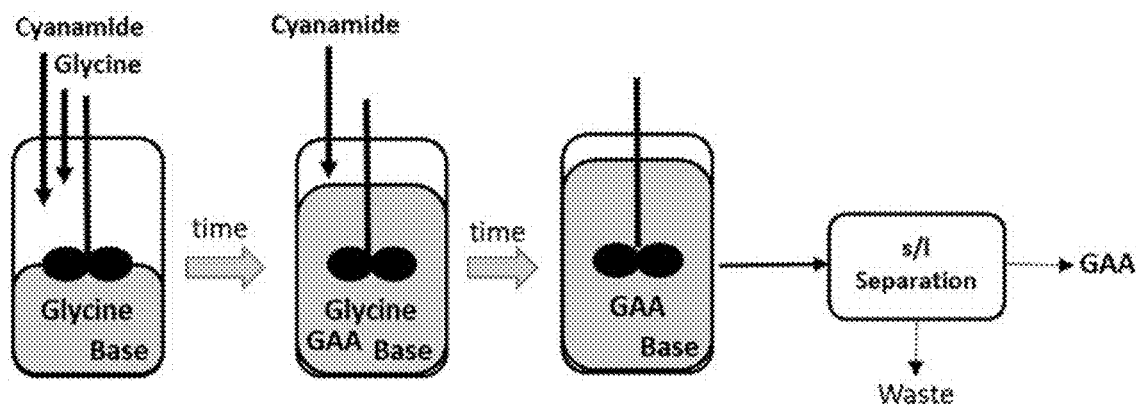

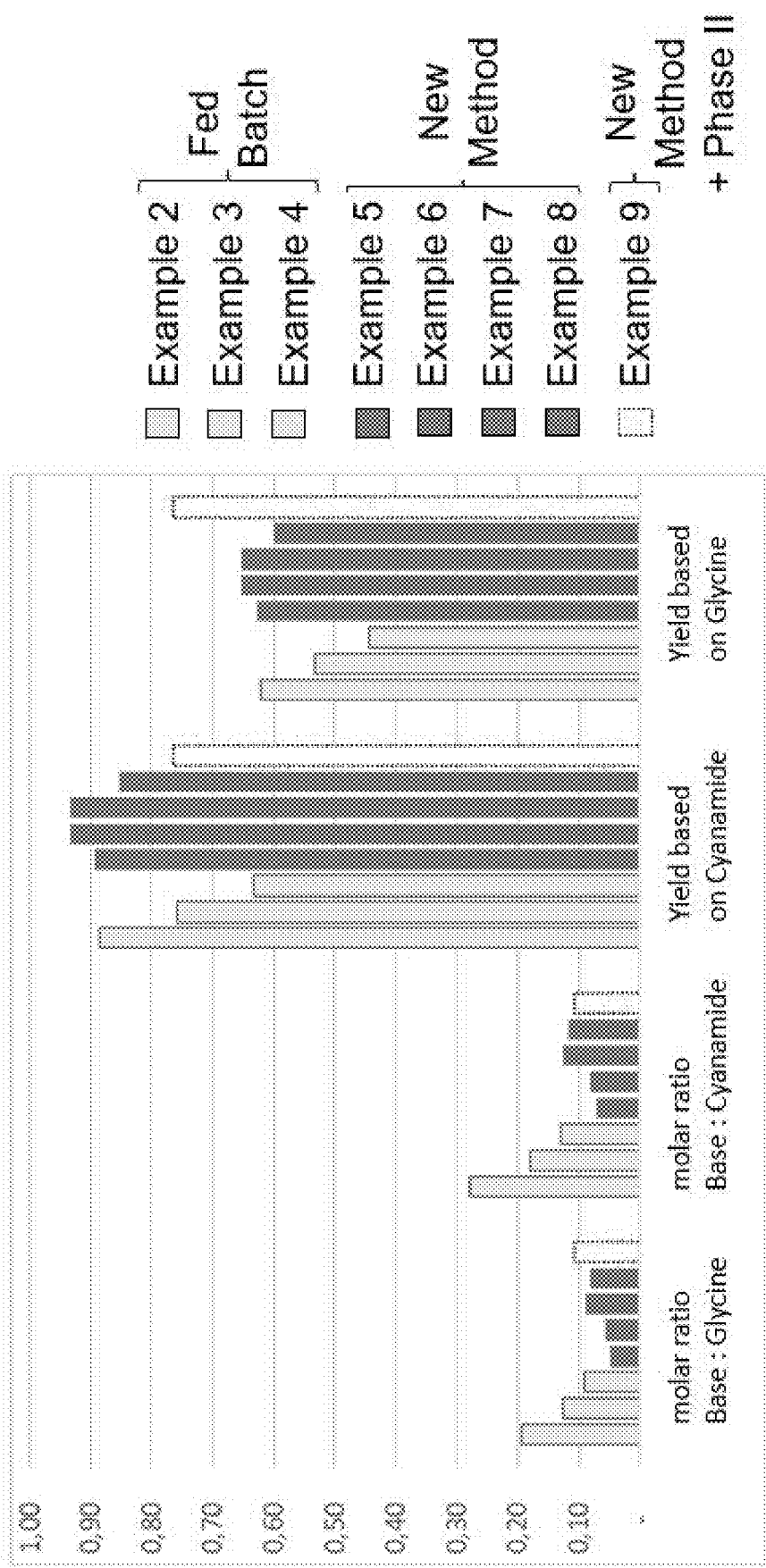
FIG. 4: Overall Results of Examples 2 - 9

METHOD FOR PREPARING GUANIDINO ACETIC ACID

CROSS-REFERENCE TO RELATED APPLICATIONS

This application is the National Stage entry under § 371 of International Application No. PCT/EP2021/072929, filed on Aug. 18, 2021, and which claims the benefit of priority to European Application No. 20193773.7, Filed on Sep. 1, 2020. The content of each of these applications is hereby incorporated by reference in its entirety.

BACKGROUND OF THE INVENTION

Field of the Invention

Guanidino acetic acid (GAA) is a colorless crystalline organic compound used as animal feed additive (e.g., WO2005120246 A1 and US2011257075 A1). GAA is a natural precursor of creatine (e.g. Humm et al., Biochem. J. (1997) 322, 771-776). Therefore, the supplementation of GAA allows for an optimal supply of creatine in the organism.

Description of Related Art

The present invention concerns an improved method for preparing guanidino acetic acid (GAA) by reacting cyanamide with glycine in an aqueous reaction mixture in the presence of a base.

The production of GAA by adding cyanamide to glycine was first described in 1861 (M. Strecker, comptes rendus 1861, 52, 1212; cited in: Ber. Chem. Ges. (now: Eur. J. Inorg. Chem.) 1908, 41, 4385). A weakly alkaline aqueous ammonia solution was used as the reaction medium. More recent publications also include reaction conditions with sodium hydroxide, sodium bicarbonate, or sodium carbonate as the base for setting the pH (e.g., CN 102329250 A and CN 101462983 A).

An alkaline environment (pH 8-10) is necessary for the production of GAA from cyanamide and glycine. In an alkaline environment, undesirable by-products of cyanamide, such as dicyandiamide, ammonia, and urea, are also formed (Buchanan and Barsky, J. Am. Chem. Soc. Vol. 52, 195, 1930). An excess of glycine can be used for suppression. Two GAA production methods from cyanamide and glycine are described in the literature:
  A) Adding a cyanamide solution to an alkaline glycine solution (fed batch; FIG. 1)
  B) Addition of glycine and cyanamide in a continuously operated reaction system with continuous recirculation of the glycine-containing mother liquor after product separation. In the process the glycine concentration is set higher than the cyanamide concentration (FIG. 2).
  A) Fed-Batch: A large amount of base is necessary to adjust the pH value, because the glycine provided has an unfavorable pH buffering effect. During the reaction, however, glycine is consumed and the buffer effect diminishes, the pH rises too high and worsens the yield and selectivity. This undesired effect can be prevented by adding acid, but has not yet been described. The pH control with acid leads to an overall high rate of salt formation.
  B) Continuously operated reaction system: For technical reasons, continuous operation allows only a small excess of glycine in the reactor (typically: glycine:cyanamide=2:1), otherwise the circuit becomes too large. This results in poor selectivities. At the same time, by-products have to leave the cycle, otherwise there is a risk of accumulation. However, such a purge stream also removes large amounts of glycine, which are then lost.

Both process variants presented come with disadvantages. High selectivities can only be achieved in a batch process, but relatively high amounts of base are necessary for good reaction performance.

SUMMARY OF THE INVENTION

The problem to be solved by the present invention is to provide a method for preparing guanidino acetic acid (GAA) by reacting cyanamide with glycine in an aqueous reaction mixture in the presence of a base that avoids high molar amounts of base or acid for pH control under maintaining the reaction selectivity and product yield.

This is achieved by a method for preparing guanidino acetic acid (GAA) from cyanamide and glycine, wherein cyanamide and glycine are continuously added to a pre-mixed aqueous solution comprising glycine and base characterized in that the rate of addition of cyanamide and glycine is adjusted such that the molar ratio of base to glycine within the reaction mixture is kept constant at 0.1 to 0.4 over the entire reaction period.

BRIEF DESCRIPTION OF THE DRAWINGS

FIG. 1 shows a fed batch.
FIG. 2 shows a continuously operated reaction system.
FIG. 3 shows a fed batch concept according to the present invention.
FIG. 4 shows overall results of Examples 2-9.

DETAILED DESCRIPTION OF THE INVENTION

Suitable bases for the method according to the present invention are e.g. the hydroxides, the bicarbonates, or the carbonates of potassium or sodium.

In the method according to the present invention as described above, glycine is used as both, reagent and acid regulator. Therefore, the further addition of base, such as sodium hydroxide (NaOH), is avoided. Due to this particular reaction control the very high molar glycine:cyanamide ratio allow for high selectivities. Typical glycine:cyanamide ratios for a reaction according to the present invention in the moment when cyanamide and glycine are added to the reaction mixture are up to 100:1, whereas in conventional continuous processes the glycine:cyanamide ratios in the moment when cyanamide and glycine are added to the reaction mixture are below 5:1 leading to unwanted side products, such as dicyandiamide, ammonia, and melamine.

In a particular embodiment of the method according to the present invention cyanamide is reacted with an overall equimolar amount of glycine, wherein in a subsequent step ("Phase II" of the reaction) the remaining molar amount of cyanamide without glycine is continuously added to the glycine containing reaction mixture under maintaining the pH of the reaction mixture below 10 by adding an acid.

The pH of the reaction mixture may be measured by means of an electronic pH meter or by means of pH indicator paper.

The reaction Phase II does not only allow for full cyanamide conversion, but also for full glycine conversion (cf. Example 9).

The acid added to the reaction mixture for pH control may be *sulphurous* acid, acetic acid, hydrochloric acid, carbonic acid, formic acid or phosphorous acid, preferably acetic and *sulphurous* acid.

In a further embodiment cyanamide and glycine are simultaneously added to the reaction mixture in the form of a mixture comprising both, cyanamide and glycine.

EXPERIMENTAL PART

General Information
Suppliers and devices used in experiment 1:
Glycine, p.a.: Merck KGaA, Darmstadt (Germany)
Hydrochloric acid (aq.): Merck KGaA, Darmstadt (Germany)
Formic acid: Merck KGaA, Darmstadt (Germany)
Cyanamide 50% in $H_2O$: ABCR GmbH, Karlsruhe (Germany)
Sodium hydroxide: Merck KGaA, Darmstadt (Germany)
Membrane pump Fink Ritmo R05
Piston pump Ismatec
KPG Stirrer
Suppliers used for all other experiments:
Glycine, p.a.: Evonik Rexim (Nanning) Pharmaceutical Co. Ltd., Nanning (China)
Sodium hydroxide 50% in $H_2O$: VWR International, Radnor (USA)
Cyanamide 50% in $H_2O$: Brenntag, Essen (Germany)
Analytics:
GAA analysis via Agilent HPC
  Derivatization: none
  Column: Zorbax SB-Phenyl; column temperature: 30° C.
  UV-Detection at 200 nm
  Eluent: 1780 g $H_2O$+68 g ortho-phosphoric acid 85 wt.-% in $H_2O$
  Flow: 0.4 mL/min
  Retention time: 15.1 min
The pH of the reaction mixture may be measured by means of an electronic pH meter or by means of pH indicator paper.

Example 1

Identification of Best pH-Value for the Reaction of Cyanamide with Glycine to Form Guanidino Acetic Acid (GAA)

Semi-batch trials were conducted to identify the best pH-value for the synthesis of guanidino acetic acid (GAA). For these experiments, glycine (32 g, 0.42 mol, 2.0 equiv.) in water (variable amount to adjust total glycine concentration) was placed in a 250 mL four-necked flask, equipped with a condenser, KPG-stirrer, thermometer, and pH-electrode. The pH-value was carefully adjusted by either NaOH aqueous solution (40 wt-% in $H_2O$), NaOH, HCl (aq.), or formic acid, thereby ending up with a total glycine concentration of 30 wt-%.

Cyanamide (50 wt-% in $H_2O$, 18 g, 0.21 mol, 1.0 equiv.) was added dropwise (v=1 mL/min, t=ca. 24 min) at 80° C. under stirring. After 2 h at 75° C., the formed suspension was filtered, and the wet cake was dried. HPLC analysis of the dry cake was performed to determine the GAA purity, and to calculate the yield.

The results for different pH values are shown in Table 1.

TABLE 1

| pH value | yield GAA [%] |
|---|---|
| 8.0 | 63.6 |
| 9.0 | 81.6 |
| 9.6 | 82.9 |
| 10.0 | 78.8 |
| 11.0 | 45.0 |

Very poor yields were obtained with pH values <8 or pH values >11 (not shown).

Example 2

Semi-Batch at 19 GLY-Mol-% NaOH

In a 50 L reaction device, cyanamide (50 wt-% in $H_2O$, 4.5 kg, 54 mol, 1.0 equiv., 24 mL/min for 178 min) was added to a solution of glycine (5.8 kg, 77 mol, 1.4 equiv.) and sodium hydroxide (50 wt-% in $H_2O$, 1.2 kg, 15 mol) in water (16 kg, glycine content of solution: 25 wt-%) at 82° C. under stirring. After stirring for another 2 h at 82° C. the GAA yield was determined by HPLC analysis of the formed suspension.
GAA yield: 88% (5.6 kg).
NaOH molar content in respect of glycine: 19%
pH value at reaction start: 9, pH value at reaction end: 10.

Example 3

Semi-Batch at 13 GLY-Mol-% NaOH

In a 50 L reaction device, cyanamide (50 wt-% in $H_2O$, 4.5 kg, 54 mol, 1.0 equiv., 24 mL/min for 178 min) was added to a solution of glycine (5.8 kg, 77 mol, 1.4 equiv.) and sodium hydroxide (50 wt-% in $H_2O$, 0.77 kg, 9.7 mol) in water (17 kg, glycine content of solution: 25 wt-%) at 82° C. under stirring. After stirring for another 2 h at 82° C. the GAA yield was determined by HPLC analysis of the formed suspension.
GAA yield: 76% (4.8 kg).
NaOH molar content in respect of glycine: 13%
pH value at reaction start: 9, pH value at reaction end: 9.5.

Example 4

Semi-Batch at 9 GLY-Mol-% NaOH

In a 50 L reaction device, cyanamide (50 wt-% in $H_2O$, 4.5 kg, 54 mol, 1.0 equiv., 24 mL/min for 178 min) was added to a solution of glycine (5.8 kg, 77 mol, 1.4 equiv.) and sodium hydroxide (50 wt-% in $H_2O$, 0.56 kg, 7.0 mol) in water (17 kg, glycine content of solution: 25 wt-%) at 82° C. under stirring. After stirring for another 2 h at 82° C. the GAA yield was determined by HPLC analysis of the formed suspension.
GAA yield: 63% (4.0 kg).
NaOH molar content in respect of glycine: 9%
pH value at reaction start: 8.9, pH value at reaction end: 9.3.

Example 5

Method According to the Present Invention
At 5 GLY-Mol-% NaOH, with 20% Glycine Content in Reactor at Start In a 50 L reaction device, both cyanamide (50 wt-% in $H_2O$, 4.5 kg, 54 mol, 1.0 equiv., 24 mL/min for 178 min) and a solution of glycine (4.6 kg, 62 mol, 1.1 equiv.) in water (14 kg, glycine content of solution: 25 wt-%, in total 107 mL/min for 178 min) were added to a solution of glycine (1.2 kg, 15 mol, 0.28 equiv.) and sodium hydroxide (50 wt-% in H$_2$O, 0.30 kg, 3.8 mol) in water (3.2 kg, glycine content of solution: 25 wt-%) at 82° C. under stirring. After stirring for another 2 h at 82° C. the GAA yield was determined by HPLC analysis of the formed suspension.

GAA yield: 89% (5.7 kg).

NaOH molar content in respect of glycine: 5% pH value at reaction start: 9.5, pH value at reaction end: 8.9.

Example 6

Method According to the Present Invention

At 6 GLY-Mol-% NaOH, with 30% Glycine Content in Reactor at Start

In a 50 L reaction device, both cyanamide (50 wt-% in H$_2$O, 4.5 kg, 54 mol, 1.0 equiv., 24 mL/min for 178 min) and a solution of glycine (4.0 kg, 54 mol, 1.0 equiv.) in water (12 kg, glycine content of solution: 25 wt-%, in total 93 mL/min for 178 min) were added to a solution of glycine (1.7 kg, 23 mol, 0.42 equiv.) and sodium hydroxide (50 wt-% in H$_2$O, 0.35 kg, 4.4 mol) in water (4.8 kg, glycine content of solution: 25 wt-%) at 82° C. under stirring. After stirring for another 2 h at 82° C. the GAA yield was determined by HPLC analysis of the formed suspension.

GAA yield: 93% (5.9 kg).

NaOH molar content in respect of glycine: 6% pH value at reaction start: 9.3, pH value at reaction end: 9.0.

Example 7

Method According to the Present Invention

At 9 GLY-Mol-% NaOH, with 20% Glycine Content in Reactor at Start, Cyanamide 30 wt-% in H$_2$O In a 50 L reaction device, both cyanamide (30 wt-% in H$_2$O, 7.6 kg, 54 mol, 1.0 equiv., 42 mL/min for 178 min) and a solution of glycine (4.6 kg, 62 mol, 1.1 equiv.) and sodium hydroxide (50 wt-% in H$_2$O, 0.24 kg, 3.0 mol) in water (14 kg, glycine content of solution: 25 wt-%, in total 107 mL/min for 178 min) were added to a solution of glycine (1.2 kg, 15 mol, 0.28 equiv.) and sodium hydroxide (50 wt-% in H$_2$O, 0.30 kg, 3.8 mol) in water (3.2 kg, glycine content of solution: 25 wt-%) at 82° C. under stirring. After stirring for another 2 h at 82° C. the GAA yield was determined by HPLC analysis of the formed suspension.

GAA yield: 93% (5.9 kg).

NaOH molar content in respect of glycine: 9% pH value at reaction start: 9.1, pH value at reaction end: 9.1.

Example 8

Method According to the Present Invention

At 8 GLY-Mol-% NaOH, with 20% Glycine Content in Reactor at Start, Cyanamide 30 wt-% in H$_2$O In a 50 L reaction device, both cyanamide (30 wt-% in H$_2$O, 7.6 kg, 54 mol, 1.0 equiv., 42 mL/min for 178 min) and a solution of glycine (4.6 kg, 62 mol, 1.1 equiv.) and sodium hydroxide (50 wt-% in H$_2$O, 0.20 kg, 2.5 mol) in water (14 kg, glycine content of solution: 25 wt-%, in total 107 mL/min for 178 min) were added to a solution of glycine (1.2 kg, 15 mol, 0.28 equiv.) and sodium hydroxide (50 wt-% in H$_2$O, 0.30 kg, 3.8 mol) in water (3.2 kg, glycine content of solution: 25 wt-%) at 82° C. under stirring. After stirring for another 2 h at 82° C. the GAA yield was determined by HPLC analysis of the formed suspension.

GAA yield: 85% (5.4 kg).

NaOH molar content in respect of glycine: 8% pH value at reaction start: 8.5, pH value at reaction end: 9.5.

The results of Examples 5 to 8 are shown in Table 2 and in FIG. 4.

Example 9

Method According to the Present Invention at 11 GLY-Mol-% NaOH, with 40% Glycine Content in Reactor at Start+Reaction Phase II (Add Additional Cyanamide to a Final GLY:CA Ration of 1:1)

Reaction Phase I:

In a 50 L reaction device, both cyanamide (50 wt-% in H$_2$O, 4.5 kg, 54 mol, 0.70 equiv., 24 mL/min for 178 min) and a solution of glycine (3.5 kg, 46 mol, 0.60 equiv.) in water (11 kg, glycine content of solution: 25 wt-%, in total 79 mL/min for 178 min) were added to a solution of glycine (2.3 kg, 31 mol, 0.40 equiv.) and sodium hydroxide (50 wt-% in H$_2$O, 0.66 kg, 8.3 mol) in water (6.5 kg, glycine content of solution: 24 wt-%) at 82° C. under stirring.

Reaction Phase II:

Immediately after reaction phase I, cyanamide (50 wt-% in H$_2$O, 1.9 kg, 23 mol, 0.30 equiv., 24 mL/min for 74 min) was added under stirring at 82° C. and the pH-value of the reaction was controlled by addition of H$_2$SO$_4$ (10% in water, threshold: pH<=10). After stirring for another 5 h at 82° C. the GAA yield was determined by HPLC analysis of the formed suspension.

GAA yield based on Cyanamide: 76% (5.9 kg GAA), GAA yield based on Glycine: 76%.

NaOH molar content in respect of glycine: 11% pH value at reaction start: 10, pH value at reaction end: 10

Final GLY-concentration in process: 1.3 wt-% (aim of this experiment to keep yield high, and to minimize this value).

TABLE 2

Results of Examples 2-9

| Ex. No. | Overall Cyanamide [mol] | Overall Glycine [mol] | Overall Base [mol] | GAA [mol] | molar ratio Base: Glycine | molar ratio Base: Cyanamide | Yield based on Cyanamide | Yield based on Glycine | Molar ratio Glycine: Cyanamide |
|---|---|---|---|---|---|---|---|---|---|
| 2 | 54 | 77 | 15.0 | 47.8 | 0.19 | 0.28 | 89% | 62% | 1.4 |
| 3 | 54 | 77 | 9.7 | 41.0 | 0.13 | 0.18 | 76% | 53% | 1.4 |
| 4 | 54 | 77 | 7.0 | 34.2 | 0.09 | 0.13 | 63% | 44% | 1.4 |
| 5 | 54 | 77 | 3.8 | 48.2 | 0.05 | 0.07 | 89% | 63% | 1.4 |
| 6 | 54 | 77 | 4.4 | 50.4 | 0.06 | 0.08 | 93% | 65% | 1.4 |
| 7 | 54 | 77 | 6.8 | 50.4 | 0.09 | 0.13 | 93% | 65% | 1.4 |

TABLE 2-continued

Results of Examples 2-9

| Ex. No. | Overall Cyan- amide [mol] | Overall Glycine [mol] | Overall Base [mol] | GAA [mol] | molar ratio Base: Glycine | molar ratio Base: Cyan- amide | Yield based on Cyan- amide | Yield based on Glycine | Molar ratio Glycine: Cyan- amide |
|---|---|---|---|---|---|---|---|---|---|
| 8 | 54 | 77 | 6.3 | 46.1 | 0.08 | 0.12 | 85% | 60% | 1.4 |
| 9 | 77 | 77 | 8.3 | 58.9 | 0.11 | 0.11 | 77% | 77% | 1.0 |

Examples 2-4: Fed batch.
Examples 5-8: New method,
Example 9: New method+Phase II.

Compared to the new method, the fed-batch tests have relatively high base: raw material ratios, but at the same time no improved yields. On the contrary, the yield actually improves, which can be attributed to better control of the pH value. This applies to both, the yield based on cyanamide and glycine.

"New method+Phase II" (cf. Example 9) means that attention was paid to full conversion of the starting compounds by using glycine and cyanamide in a ratio of 1:1 based on the overall reaction, wherein in a subsequent step the remaining molar amount of cyanamide without glycine is continuously added to the glycine containing reaction mixture under maintaining the pH of the reaction mixture below 10 by adding an acid This was only made possible with the help of the new method, since the pH value can still be controlled.

The results of Examples 2-9 are also depicted in FIG. 4.

The invention claimed is:

1. A method for preparing guanidino acetic acid (GAA) from cyanamide and glycine, the method comprising:
    continuously adding the cyanamide and the glycine to a pre-mixed aqueous solution comprising the glycine and a base,
    wherein a rate of addition of the cyanamide and the glycine is adjusted such that a molar ratio of base to glycine within a reaction mixture is kept constant at 0.1 to 0.4 over an entire reaction period.

2. The method of claim 1, wherein the cyanamide is reacted with an overall equimolar amount of the glycine, and wherein subsequently, a remaining molar amount of the cyanamide without glycine is continuously added to a glycine containing reaction mixture while maintaining a pH of the reaction mixture below 10 by adding an acid.

3. The method of claim 1, wherein the cyanamide and the glycine are simultaneously added to the reaction mixture in a form of a mixture comprising both the cyanamide and the glycine.

* * * * *